United States Patent
Baheti et al.

(10) Patent No.: US 10,677,905 B2
(45) Date of Patent: Jun. 9, 2020

(54) SYSTEM AND METHOD FOR OCCUPANCY DETECTION USING A MILLIMETER-WAVE RADAR SENSOR

(71) Applicant: Infineon Technologies AG, Neubiberg (DE)

(72) Inventors: Ashutosh Baheti, Munich (DE); Reinhard-Wolfgang Jungmaier, Aying (DE); Avik Santra, Munich (DE); Saverio Trotta, Munich (DE); Raghavendran Vagarappan Ulaganathan, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 254 days.

(21) Appl. No.: 15/716,175

(22) Filed: Sep. 26, 2017

(65) Prior Publication Data

US 2019/0094350 A1 Mar. 28, 2019

(51) Int. Cl.
| | |
|---|---|
| *G01S 13/04* | (2006.01) |
| *G01S 13/32* | (2006.01) |
| *A61B 5/024* | (2006.01) |
| *A61B 5/0205* | (2006.01) |
| *G01S 13/34* | (2006.01) |

(Continued)

(52) U.S. Cl.
CPC ............ *G01S 13/04* (2013.01); *A61B 5/024* (2013.01); *A61B 5/0205* (2013.01); *A61B 5/0507* (2013.01); *G01S 13/32* (2013.01); *G01S 13/34* (2013.01); *G01S 13/56* (2013.01); *A61B 5/05* (2013.01); *A61B 5/08* (2013.01);

(Continued)

(58) Field of Classification Search
CPC .......... G01S 13/04; G01S 13/32; G01S 13/34; G01S 13/56
See application file for complete search history.

(56) References Cited

U.S. PATENT DOCUMENTS

| | | |
|---|---|---|
| 7,596,241 B2 | 9/2009 | Rittscher et al. |
| 8,228,382 B2 | 7/2012 | Pattikonda |

(Continued)

FOREIGN PATENT DOCUMENTS

| | | |
|---|---|---|
| DE | 102007054507 A1 | 5/2009 |
| WO | 2008001092 A2 | 1/2008 |
| WO | 2013009473 A2 | 1/2013 |

OTHER PUBLICATIONS

Deacon, Peter et al., "Frequency Modulated Continuous Wave (FMCW) Radar," Design Team 6 Technical Lecture, Nov. 9, 2011, 27 pages.

(Continued)

*Primary Examiner* — Marc Anthony Armand
(74) *Attorney, Agent, or Firm* — Slater Matsil, LLP

(57) ABSTRACT

According to an embodiment, a method for presence detection includes performing a first scanning comprising scanning a first area using a millimeter-wave radar sensor to produce a first set of radar data; identifying a first set of targets based on the first set of radar data; performing a second scanning comprising scanning portions of the first area corresponding to the first set of targets using the millimeter-wave radar sensor, and performing micro-Doppler measurements on the portions of the first area; and determining which targets of the first set of targets meet a first set of criteria based on the micro-Doppler measurements.

22 Claims, 11 Drawing Sheets

(51) Int. Cl.
*A61B 5/05* (2006.01)
*G01S 13/56* (2006.01)
*A61B 5/08* (2006.01)
*A61B 5/00* (2006.01)

(52) U.S. Cl.
CPC .......... *A61B 5/0816* (2013.01); *A61B 5/7264* (2013.01); *A61B 2562/0257* (2013.01)

(56) References Cited

U.S. PATENT DOCUMENTS

| | | |
|---|---|---|
| 9,495,600 B2 | 11/2016 | Heu et al. |
| 2003/0179127 A1 | 9/2003 | Wienand |
| 2006/0067456 A1 | 3/2006 | Ku et al. |
| 2010/0207805 A1 | 8/2010 | Haworth |
| 2013/0113647 A1* | 5/2013 | Sentelle ................ G01S 13/32 342/22 |
| 2015/0309166 A1 | 10/2015 | Sentelle et al. |
| 2015/0369911 A1* | 12/2015 | Mabrouk ................ G01S 7/415 342/118 |
| 2017/0097413 A1 | 4/2017 | Gillian et al. |
| 2019/0137606 A1* | 5/2019 | Buddendick ............ G01S 13/42 |

OTHER PUBLICATIONS

Guercan, Yalin "Super-resolution Algorithms for Joint Range-Azimuth-Doppler Estimation in Automotive Radars," Technische Universitet Delft, TUDelft University of Technology Challenge for the Future, Jan. 25, 2017, 72 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Suleymanov, Suleyman "Design and Implementation of an FMCW Radar Signal Processing Module for Automotive Applications," Master Thesis, University of Twente, Aug. 31, 2016, 61 pages.

Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, Apr. 2014, 11 pages.

* cited by examiner

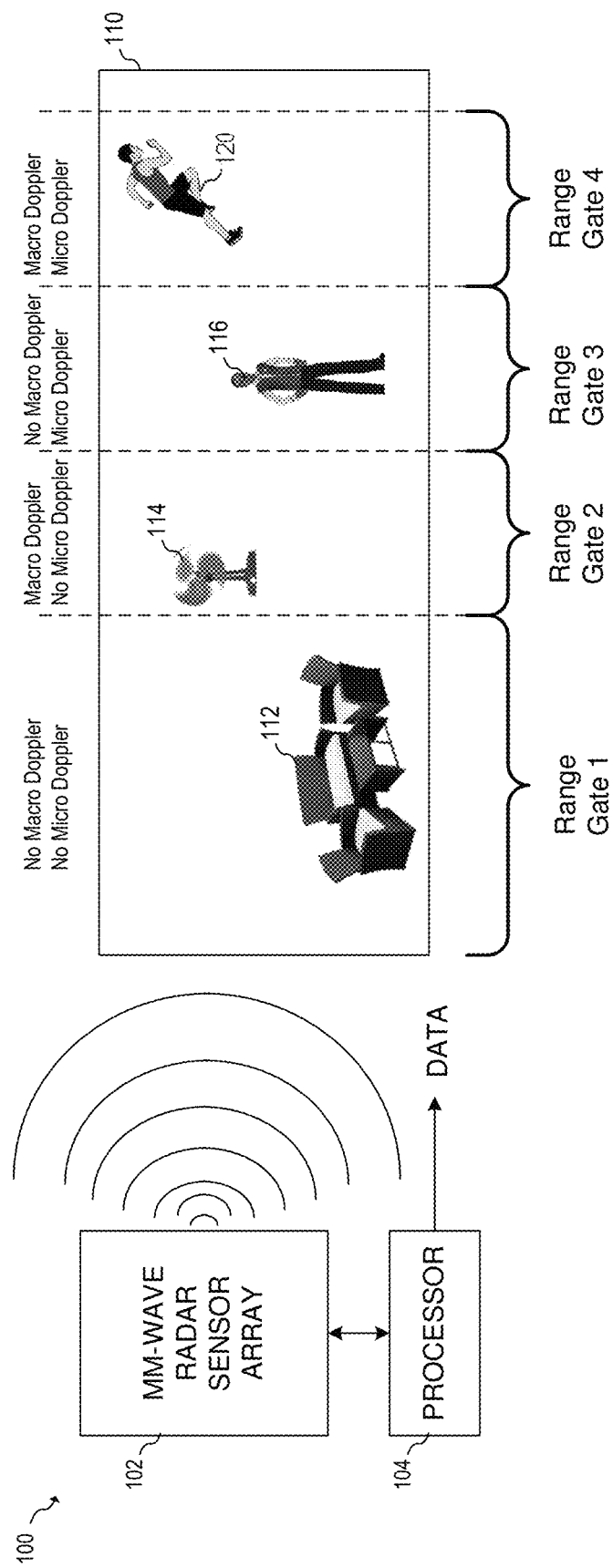

| Algorithm Stages | Furniture | Fan | Static Human | Moving Human |
|---|---|---|---|---|
| Coarse Target Detection | ☑ | ☑ | ☑ | ☑ |
| Macro Doppler Filtering | ☒ | ☒ | ☒ | ☑ |
| Micro Doppler Sensing | ☒ | N/A | ☑ | N/A |
| Classifier Stage | ☒ | ☒ | ☒ | ☑ |
| Human Detected | ☒ | ☒ | ☑ | ☑ |

SYSTEM AND METHOD FOR OCCUPANCY DETECTION USING A MILLIMETER-WAVE RADAR SENSOR

TECHNICAL FIELD

The present invention relates generally to a system and method for occupancy detection using a millimeter-wave radar sensor.

BACKGROUND

Applications in the millimeter-wave frequency regime have gained significant interest in the past few years due to the rapid advancement in low cost semiconductor technologies such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at 60 GHz, 77 GHz, and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal, and determining a distance based on a time delay and/or frequency difference between the transmission and reception of the frequency modulated signal. Accordingly, some radar systems include a transmit antenna to transmit the RF signal, a receive antenna to receive the RF, as well as the associated RF circuitry used to generate the transmitted signal and to receive the RF signal. In some cases, multiple antennas may be used to implement directional beams using phased array techniques. A MIMO configuration with multiple chipsets can be used to perform coherent and non-coherent signal processing, as well.

SUMMARY

In accordance with a preferred embodiment, a method for presence detection includes performing a first scanning comprising scanning a first area using a millimeter-wave radar sensor to produce a first set of radar data; identifying a first set of targets based on the first set of radar data; performing a second scanning comprising scanning portions of the first area corresponding to the first set of targets using the millimeter-wave radar sensor, and performing micro-Doppler measurements on the portions of the first area; and determining which targets of the first set of targets meet a first set of criteria based on the micro-Doppler measurements For a more complete understanding of the present invention, and the advantages thereof, reference is now made to the following descriptions taken in conjunction with the accompanying drawings, in which:

FIG. 1A illustrates an embodiment occupancy detection system; FIG. 1B illustrates a table showing an example of how objects are classified by an embodiment occupancy detection system;

Figure 2A:
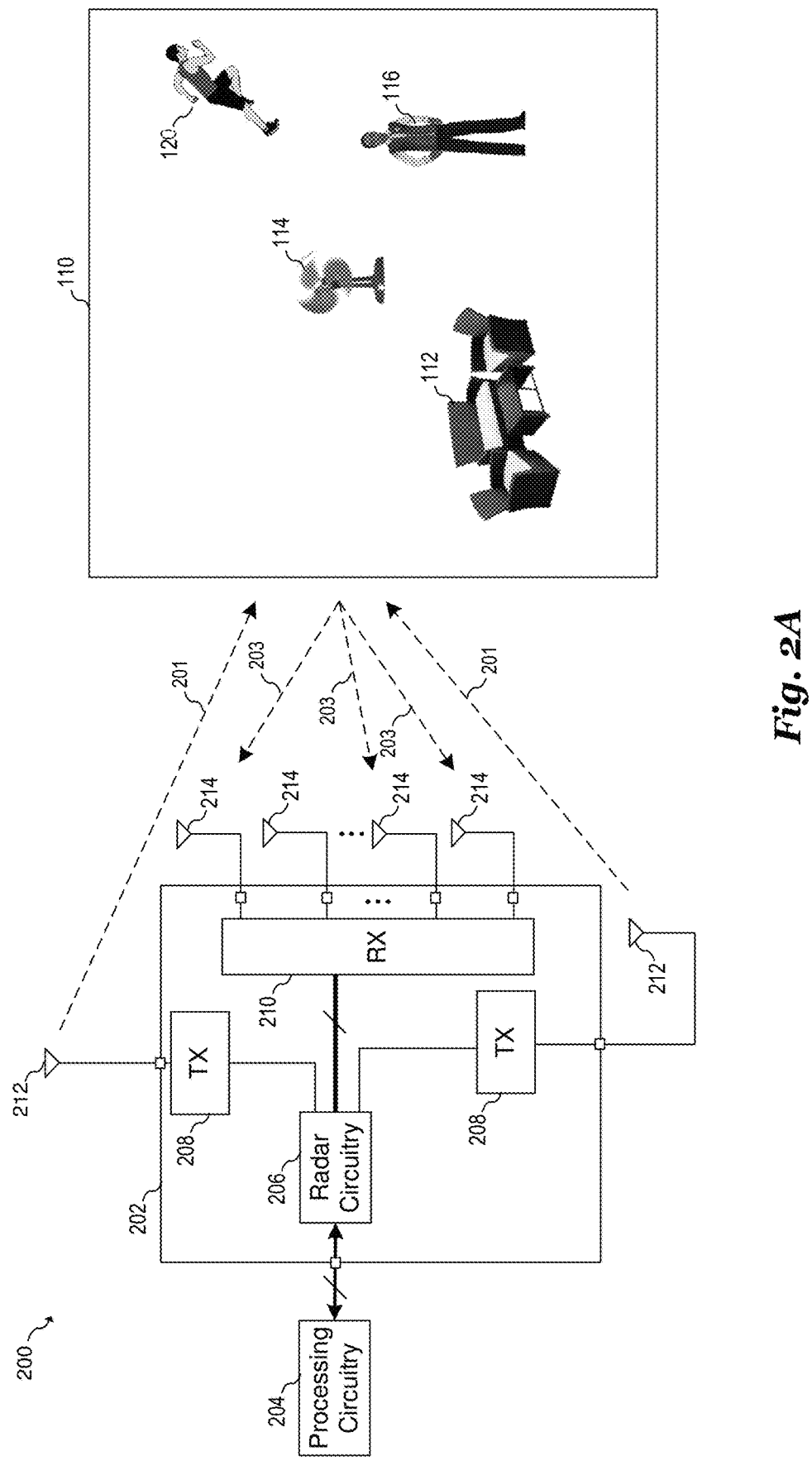
FIG. 2A illustrates a block diagram of an embodiment millimeter-wave radar sensor.

Corresponding numerals and symbols in different figures generally refer to corresponding parts unless otherwise indicated. The figures are drawn to clearly illustrate the relevant aspects of the preferred embodiments and are not necessarily drawn to scale. To more clearly illustrate certain embodiments, a letter indicating variations of the same structure, material, or process step may follow a figure number.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, a system and method for occupancy detection using a millimeter-wave radar sensor. The invention may also be applied to other RF-based systems and applications that perform detect the presence of one or more objects.

In embodiments of the present invention, a millimeter-wave based sensor is used to detect the presence of people in an area by extracted vital signs, such as heart rate and respiration, from radar measurements. If a detected object is determined to exhibit motion consistent with a heart rate and respiration of a typical human being, the detected object is classified as being human by the occupancy detection systems. During operation, the millimeter-wave radar sensor first performs a coarse measurement using macro-Doppler techniques to determine the presence of moving and non-moving objects. (In some embodiments, non-vital motion is categorized using macro-Doppler techniques.) Next, the millimeter-wave radar system performs a series of more targeted measurements of the detected objects using micro-Doppler techniques to determine whether these detected objects exhibit a heart-rate and respiration within the expected range of a human being. Based on these measurements, an embodiment system can detect the number of human beings within the measured area. In addition, embodiment systems can use millimeter-wave measurements to classify the identity of detected objects. Embodiment radar signal processing techniques can also be used to distinguish human beings from other moving objects such as animals, robots, machinery and the like.

Advantages of embodiment occupancy detection systems include, for example, the ability to detect the presence of people and objects in darkness and poor lighting conditions, and to perform radar-based occupancy detection in a computationally efficient manner.

FIG. 1A illustrates a block diagram of radar-based occupancy system 100. As shown, radar-based occupancy system 100 includes a millimeter-wave radar sensor 102, and a processor 104 that controls the operation of millimeter-wave radar sensor 102 and performs various radar signal processing operations on the data produced by millimeter-wave radar sensor 102. During operation, millimeter-wave radar sensor 102 transmits millimeter-wave RF signals that are reflected by various objects 112, 114, 116 and 120 present within area 110. These received RF signals are converted to a digital representation and processed by processor 104 to determine, for example, the number of human beings within area 110, and/or to identify, motion or classification of objects 112, 114, 116 and 120 within area 110. The result of this processing produces various data (represented by signal DATA) indicative of the presence and classification of the various objects 112, 114, 116 and 120 within area 110.

As shown, the objects within area 110 are represented as furniture 112, a fan 114, a static human 116 and a moving human 120 for the purpose of illustration. It should be understood that in the various embodiments of the present invention, other object types and/or can be detected by embodiment radar-based occupancy systems. For example, embodiment radar-based occupancy detection systems can be used to detect the presence and count the number of animals, robots, machinery and other objects within a particular area. Area 110 represents any finite area within the field of view of millimeter-wave radar sensor 102 and may represent, for example, a conference room, office, automobile, store, public area, private area, or any other physical area in which the presence of objects are detected.

In some embodiments, objects 112, 114, 116 and 120 within area 110 are detected and identified using a two-step process. In the first step, a coarse identification is performed that detects the location and motion of each object 112, 114, 116 and 120. During this coarse identification process, each object 112, 114, 116 and 120 are resolved within discrete range gates. While four range gates are shown in FIG. 1A for the purpose of illustration, it should be understood that any number of range-gates can be used depending on the particular embodiment and its specifications. In addition to locating each object within range-gates, the radar-based occupancy system performs a macro-Doppler analysis of the radar data produced by millimeter-wave radar sensor 102 to determine the motion of each object. In embodiments that utilize a frequency modulated continuous wave (FMCW) radar sensor, the location of each object 112, 114, 116 and 120 within a range-gate may be found by taking a range FFT of the baseband radar signal produced by millimeter-wave radar sensor 102, and the motion of the various objects may be determined, for example, by taking a further FFTs to determine each object's velocity using Doppler analysis techniques known in the art. In embodiments in which millimeter-wave radar sensor 102 includes a receive antenna array, further FFTs may also be used to determine the azimuth of each object 112, 114, 116 and 120 with respect to millimeter-wave radar sensor 102. In the illustrated example, furniture 112 is identified in range-gate 1 as being a static object, fan 114 is identified in range-gate 2 as being a moving object, static human 116 is identified in range-gate 3 as being a static object and moving human 120 is identified in range-gate 4 as being a moving object.

In the second step, micro-Doppler techniques are used to detect small motions of each object 112, 114, 116 and 120. These small detected motions are analyzed to determine whether these motions are indicative of the heart rate and respiration of a human being. During the second step, millimeter-wave radar sensor 102 makes a series of radar measures that are more specifically directed toward each object 112, 114, 116 and 120. For example, in embodiments in which millimeter-wave radar sensor 102 includes a transmit antenna array, these directed measurements are performed by steering the radar beam produced by millimeter-wave radar sensor 102 using phase-array radar techniques. Based on these more directed radar measurements made during the second step, processor 104 determines whether each object 112, 114, 116 and 120 experiences small motions consistent with human vital signs such as heart rate and respiration. In the illustrated example, furniture 112 is identified in range-gate 1 as a static object, fan 114 is identified in range-gate 2 as a moving object, static human 116 is identified in range-gate 3 as a static object and moving human 120 is identified in range-gate 4 as a moving object.

FIG. 1B illustrates a table showing a summary of how an embodiment millimeter-wave-based radar occupancy detection system might classify objects 112, 114, 116 and 120 shown in FIG. 1A. As shown, furniture 112 is not recognized as a moving object and does not exhibit human-like vital signs; fan 114 is recognized as a moving object, but does not exhibit human-like vital signs as measured by millimeter-wave radar sensor 102; and moving human 120 is recognized as a human object via a macro-Doppler classifier, meaning that the motion of moving human 120 exhibits human-like motion. Static human 116 is not recognized as a moving object but exhibits human-like vital signs.

FIG. 2A illustrates a block diagram of a millimeter-wave radar sensor system 200 that may be used to implement millimeter-wave radar sensor circuits in the various disclosed embodiments. Millimeter-wave radar sensor system 200 includes millimeter-wave radar sensor circuit 202 and processing circuitry 204. Embodiment millimeter-wave radar sensor circuits may be implemented, for example, using a two-dimensional millimeter-wave phase-array radar that measures the position and relative speed of objects 112, 114, 116 and 120. The millimeter-wave phase-array radar transmits and receives signals in the 20 GHz to 122 GHz range. Alternatively, frequencies outside of this range may also be used. In some embodiments, millimeter-wave radar sensor circuit 202 operates as a frequency modulated continuous wave (FMCW) radar sensor having multiple transmit and receive channels. Alternatively, other types of radar systems may be used such as pulse radar, MCFW, and NLFM to implement millimeter-wave radar sensor circuit 202.

Millimeter-wave radar sensor circuit 202 transmits and receives radio signals for detecting the presence and motion of objects 112, 114, 116 and 120 in three-dimensional space. For example, millimeter-wave radar sensor circuit 202 transmits an incident RF signals 201 and receives RF signals 203 that are reflection of the incident RF signals from one or more of objects 112, 114, 116 and 120. The received reflected RF signals 203 is downconverted by millimeter-wave radar sensor circuit 202 to determine beat frequency signals. These beat frequency signals may be used to determine information such as the location, speed, angle, etc., of objects 112, 114, 116 and 120 in three-dimensional space. In the specific example of FMCW radar, the beat frequency is proportional to the distance between millimeter-wave radar sensor circuit 202 and the object being sensed.

In various embodiments, millimeter-wave radar sensor circuit 202 is configured to transmit incident RF signals 201 toward objects 112, 114, 116 and 120 via transmit antennas 212 and to receive reflected RF signals 203 from objects 112, 114, 116 and 120 via receive antennas 214. Millimeter-wave radar sensor circuit 202 includes transmitter front-end circuits 208 coupled to transmit antennas 212 and receiver front-end circuit 210 coupled to receive antennas 214.

During operation, transmitter front-end circuits 208 may transmit RF signals toward objects 112, 114, 116 and 120 simultaneously or individually using beamforming depending on the phase of operation. While two transmitter front-end circuits 208 are depicted in FIG. 2A, it should be appreciated that millimeter-wave radar sensor circuit 202 may include greater than two transmitter front-end circuits 208. Thus, in various embodiments, the number of transmitters can be extended to n×m. Each transmitter front-end circuit 208 includes circuitry configured to produce the incident RF signals. Such circuitry may include, for example, RF oscillators, upconverting mixers, RF amplifiers, variable gain amplifiers, filters, transformers, power splitters, and other types of circuits.

Receiver front-end circuit 210 receives and processes the reflected RF signals from objects 112, 114, 116 and 120. As shown in FIG. 2A, receiver front-end circuit 210 is configured to be coupled to four receive antennas 214, which may be configured, for example, as a 2×2 antenna array. In alternative embodiments, receiver front-end circuit 210 may be configured to be coupled to greater or fewer than four antennas, with the resulting antenna array being of various n×m dimensions depending on the specific embodiment and its specifications. Receiver front-end circuit 210 may include, for example, RF oscillators, upconverting mixers, RF amplifiers, variable gain amplifiers, filters, transformers, power combiners and other types of circuits.

Radar circuitry 206 provides signals to be transmitted to transmitter front-end circuits 208, receives signals from receiver front-end circuit 210, and may be configured to control the operation of millimeter-wave radar sensor circuit 202. In some embodiments, radar circuitry 206 includes, but is not limited to, frequency synthesis circuitry, upconversion and downconversion circuitry, variable gain amplifiers, analog-to-digital converters, digital-to-analog converters, digital signal processing circuitry for baseband signals, bias generation circuits, and voltage regulators.

Radar circuitry 206 may receive a baseband radar signal from processing circuitry 204 and control a frequency of an RF oscillator based on the received baseband signal. In some embodiments, this received baseband signal may represent a FMCW frequency chip to be transmitted. Radar circuitry 206 may adjust the frequency of the RF oscillator by applying a signal proportional to the received baseband signal to a frequency control input of a phase locked loop. Alternatively, the baseband signal received from processing circuitry 204 may be upconverted using one or more mixers. Radar circuitry 206 may transmit and digitize baseband signals via a digital bus (e.g., a USB bus), transmit and receive analog signals via an analog signal path, and/or transmit and/or receive a combination of analog and digital signals to and from processing circuitry 204.

Processing circuitry 204 acquires baseband signals provided by radar circuitry 206 and formats the acquired baseband signals for transmission to an embodiment signal processing unit. These acquired baseband signals may represent beat frequencies, for example. In some embodiments, processing circuitry 204 includes a bus interface (not shown) for transferring data to other components within the occupancy detection system. Optionally, processing circuitry 204 may also perform signal processing steps used by embodiment occupancy detection systems such as a fast Fourier transform (FFT), a short-time Fourier transform (STFT), macro-Doppler analysis, micro-Doppler analysis, vital sign analysis, object classification, machine learning, and the like. In addition to processing the acquired baseband signals, processing circuitry 204 may also control aspects of millimeter-wave radar sensor circuit 202, such as controlling the transmissions produced by millimeter-wave radar sensor circuit 202.

The various components of millimeter-wave radar sensor system 200 may be partitioned in various ways. For example, millimeter-wave radar sensor circuit 202 may be implemented on one or more RF integrated circuits (RFICs), antennas 212 and 214 may be disposed on a circuit board, and processing circuitry 204 may be implemented using a processor, a microprocessor, a digital signal processor and/or a custom logic circuit disposed on one or more integrated circuits/semiconductor substrates. Processing circuitry 204 may include a processor that executes instructions in an executable program stored in a non-transitory computer readable storage medium, such as a memory to perform the functions of processing circuitry 204. In some embodiments, however, all or part of the functionality of processing circuitry 204 may be incorporated on the same integrated circuit/semiconductor substrate on which millimeter-wave radar sensor circuit 202 is disposed.

In some embodiments, some or all portions of millimeter-wave radar sensor circuit 202 may be implemented in a package that contains transmit antennas 212, receive antennas 214, transmitter front-end circuits 208, receiver front-end circuit 210, and/or radar circuitry 206. In some embodiments, millimeter-wave radar sensor circuit 202 may be implemented as one or more integrated circuits disposed on a circuit board, and transmit antennas 212 and receive antennas 214 may be implemented on the circuit board adjacent to the integrated circuits. In some embodiments, transmitter front-end circuits 208, receiver front-end circuit 210, and radar circuitry 206 are formed on a same radar front-end integrated circuit (IC) die. Transmit antennas 212 and receive antennas 214 may be part of the radar front-end IC die, or may be implemented as separate antennas disposed over or adjacent to the radar front-end IC die. The radar front-end IC die may further include conductive layers, such as redistribution layers (RDLs), used for routing and/or for the implementation of various passive or active devices of millimeter-wave radar sensor circuit 202. In an embodiment, transmit antennas 212 and receive antennas 214 may be implemented using the RDLs of the radar front-end IC die.

Figure 2B:
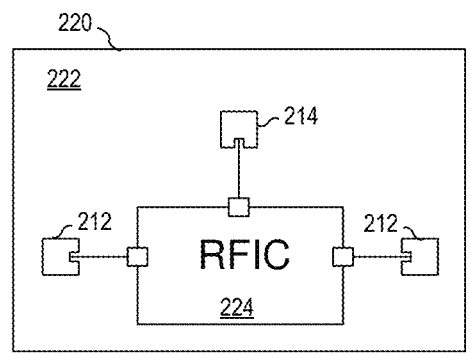
FIGS. 2B and 2C illustrate plan views of embodiment millimeter-wave radar sensor circuits.

FIG. 2B illustrates a plan view of millimeter-wave radar sensor circuit 220 that may be used to implement millimeter-wave radar sensor circuit 202. As shown, millimeter-wave radar sensor circuit 220 is implemented as an RFIC 224 coupled to transmit antennas 212 and receive antenna 214 implemented as patch antennas disposed on or within substrate 222. In some embodiments, substrate 222 may be implemented using a circuit board on which millimeter-wave radar sensor circuit 202 is disposed and on which transmit antennas 212 and receive antennas 214 are implemented using conductive layers of the circuit board. Alternatively, substrate 222 represents a wafer substrate on which one or more RDLs are disposed and on which transmit antennas 212 and receive antennas 214 are implemented using conductive layers on the one or more RDLs.

Figure 2C:
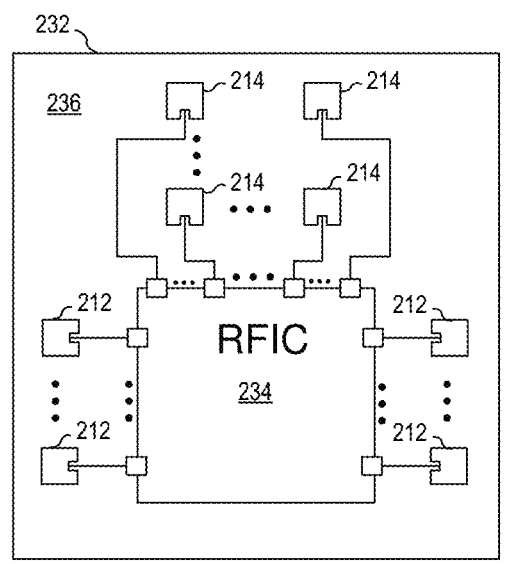

FIG. 2C illustrates a plan view of millimeter-wave radar sensor circuit 232 that includes an array of transmit antennas 212 and an array of receive antennas 214 coupled to RFIC 234 disposed on substrate 236. In various embodiments, transmit antennas 212 may form an array of m antennas and receive antennas 214 may form an array of n antennas. Each of the m transmit antennas 212 are coupled to a corresponding pin on RFIC 234 and coupled to a corresponding transmit circuit within RFIC 234; and each of the n receive antennas 214 are coupled to a corresponding pin on RFIC 234 and coupled to a corresponding receive circuit within RFIC 234. In various embodiments, the array of transmit antennas 212 and the array of receive antennas 214 may be implemented as a uniform array or a linear array of any dimension. It should be appreciated that the implementations of FIGS. 2B and 2C are just two examples of the many ways that embodiment millimeter-wave radar sensor circuits could be implemented.

Figures 3A, 3B:
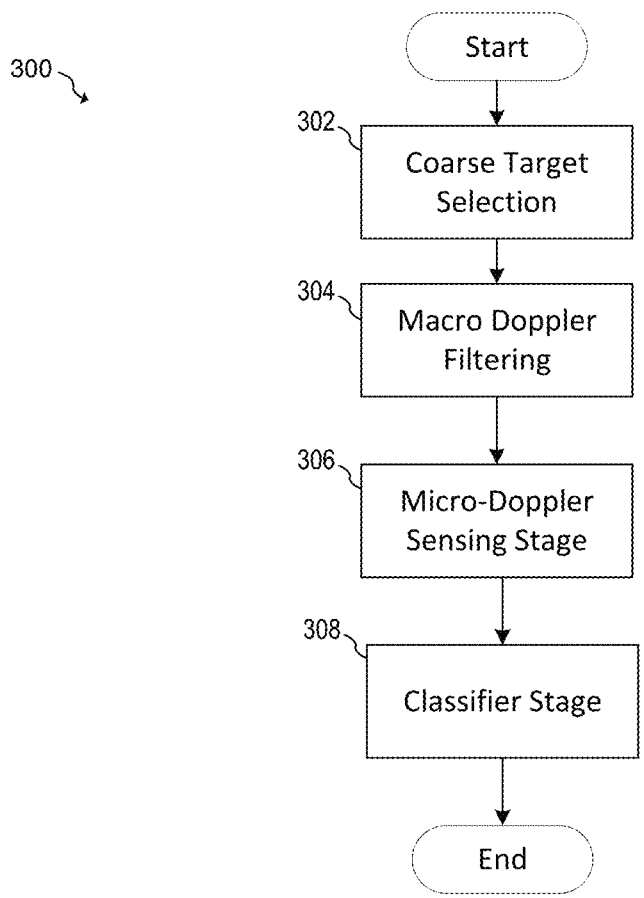
FIG. 3A illustrates an embodiment occupancy detection method.
FIG. 3B illustrates a table showing an example of how objects are classified by the embodiment occupancy detection method.

FIG. 3A illustrates a block diagram of a method 300 for detecting occupants. In step 302 a coarse target selection is performed in which a first set of targets are identified using a millimeter-wave radar sensor such as millimeter-wave radar sensors 102, 202, 220 and 232 shown in FIGS. 1A, 2A, 2B and 2C, respectively. In various embodiments that utilize FMCW radar, an FFT is taken of the baseband radar system and objects are identified within various range-gates. In some embodiments, objects detected within multiple adjacent range gates are clustered together to help prevent a single object being counted as multiple objects. In some embodiments, such as those that use multiple receive antennas, additional FFTs are performed to resolve detected objects across azimuth as well as range. During coarse target selection step 302, multiple chirps may be transmitted and received by the millimeter-wave radar sensor.

In step 304, macro-Doppler filtering is performed on the radar data used to perform the coarse target selection using macro-Doppler filtering techniques known in the art. In some embodiments a two-dimensional FFT may be taken of a range FFT over slow-time to determine the velocity of each detected object. Alternatively, the velocity of each object may be determined by other waveform techniques including, but not limited to triangular chirp and staggered pulse repetition time (PRT).

In step 306, micro-Doppler sensing is performed in which additional, more directed, radar measurements are performed to detect vital signals such as pulse and heart rate from the various objects detected in coarse target selection stage 302. Transmit beamforming using multiple antennas may be used to direct radar measurements to the identified targets based on the azimuth determinations made in coarse target selection stage 302

In step 308, identified targets are classified in order to determine the identity of detected objects based on the results of the macro-Doppler filtering. In some embodiments, the results of the macro-Doppler filtering are input to a machine learning algorithm such as, but not limited to a random forest algorithm, adaptive boosting (AdaBoost) algorithm and/or a neural network algorithm in order to identify the type of object being detected. Similarly, the vital signals determined in micro-Doppler sensing stage 306 may also be input to the machine learning algorithm in addition to the macro-Doppler data to distinguish and identify objects such as moving human beings and other objects such as robots and animals.

FIG. 3B illustrates a table shown to illustrate how the outputs of each step of method 300 shown in FIG. 3A factor into the decision as to whether or not objects 112, 114, 116 and 120 shown in FIG. 1A are identified as being human. With respect to furniture 112, the coarse target detection step 302 identifies the location of furniture 112, macro-Doppler filtering step 304 determines that furniture 112 is not moving and micro-Doppler sensing stage 306 determines that furniture 112 does not exhibit any vital signals. Therefore, classifier stage 308 determines that the furniture 112 is non-human. With respect to fan 114, the coarse target detection step 302 identifies the location of fan 114 and macro-Doppler filtering step 304 characterizes the motion of fan 114. Based on the output of macro-Doppler filtering step 304, classifier stage 308 determines that fan 114 is non-human and a micro-Doppler analysis is not performed. In an alternative embodiment, a micro-Doppler analysis may also be performed on fan 114.

With respect to static human 116, the coarse target detection step 302 identifies the location of static human 116 and macro-Doppler filtering step 304 characterizes static human 116 as not moving and micro-Doppler sensing stage 306 determines that static human 116 exhibits vital signals within the expected range of a human being. Therefore, classifier stage 308 determines that static human 116 is human.

With respect to moving human 120, the coarse target detection step 302 identifies the location of moving human and macro-Doppler filtering step 304 characterizes the motion of moving human. Based on the output of macro-Doppler filtering step 304, classifier stage 308 determines that the moving human is, in fact, human and a micro-Doppler analysis is either not performed or not analyzed. In an alternative embodiment, a micro-Doppler analysis may also be performed on moving human 120.

Figure 4A:
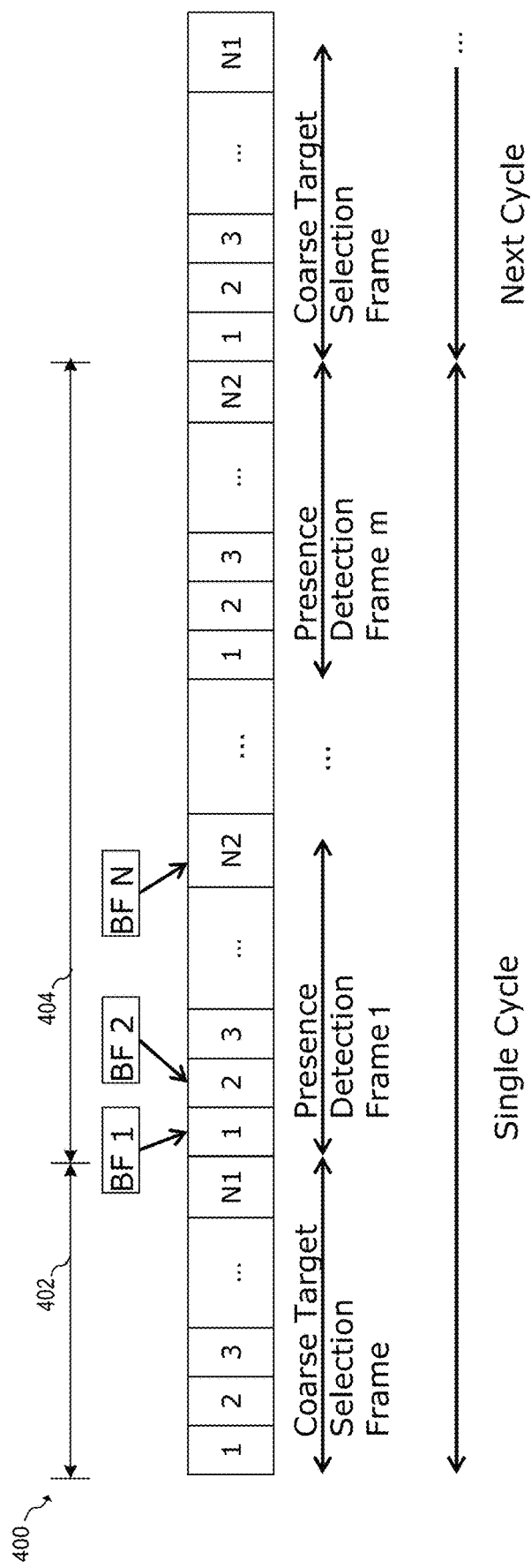
FIGS. 4A, 4B and 4C show a frame diagrams illustrating a sequences of transmitted chirps according to embodiments of the present invention.

FIG. 4A shows a frame diagram 400 that illustrates a sequence of transmitted chirps according to an embodiment of the present invention. As shown, each embodiment detection cycle includes a coarse target selection frame during which the presence of various objects are detected, and m presence detection frames during which micro-Doppler detection is performed on detected objections. The coarse target selection frame may occur during a first scanning 402 and the presence detection frames may occur during a second scanning 404. In some embodiments, each of the m presence detection frames corresponds to a different detected object. In each of the m presence detection frames, beamforming is used to direct an RF beam towards the object being detected. In alternative embodiments, there may not be a one-to-one correspondence between the number of detected objects and the number of presence detection frames. Such a situation may arise, for example, when a non-human object is identified while performing the coarse target selection and/or when one that one detected object is visible within a single RF beam during the presence detection phase.

Figure 4B:
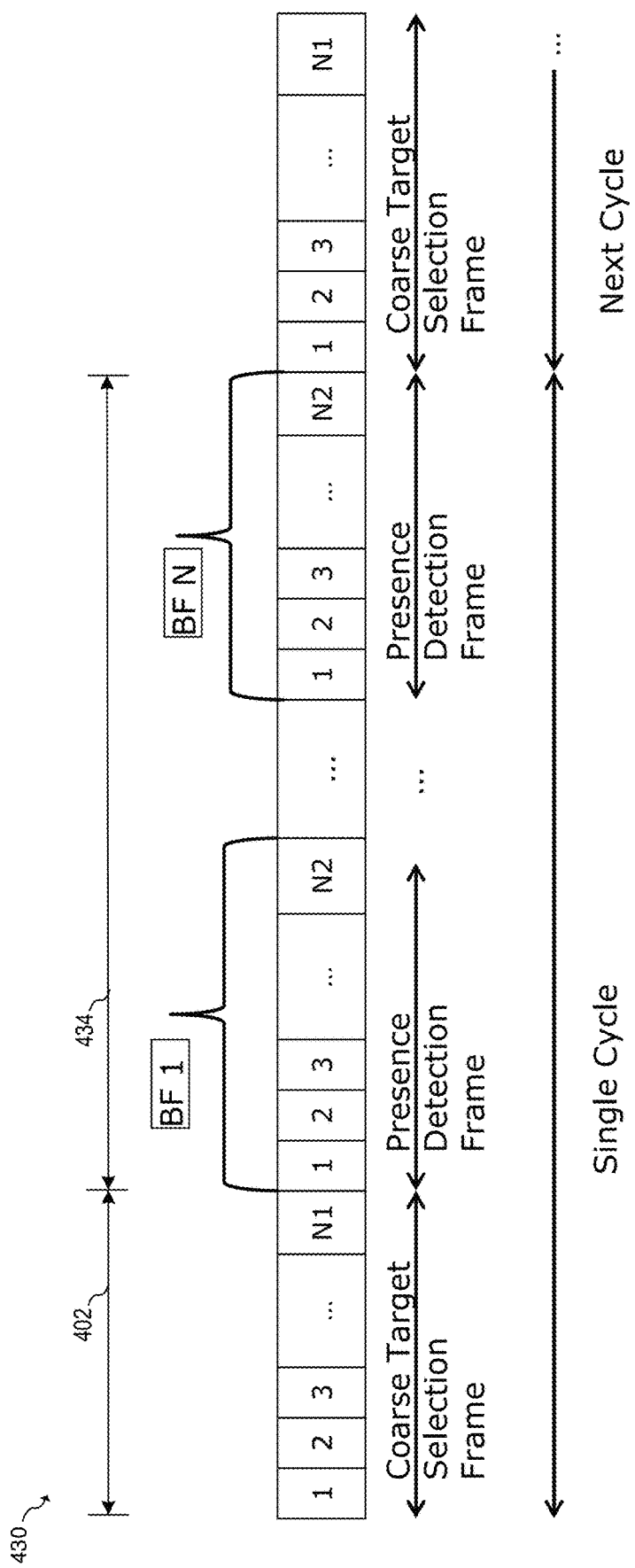

The coarse target selection frame includes N1 chirps, where N1 may be within a range of values from 16 to N according to the illustrated embodiment. In some embodiments, N is power of two in order to accommodate the use of FFTs in the processing of the radar data. N2 is the number of chips used during the presence detection frame. The number of chirps N2 may be adaptively selected according to the number of objects/targets identified during the coarse target selection phase. In some embodiments, the number of chirps N2 depends on the number of potential targets identified in the coarse target selection frame. In alternative embodiments, the presence detection frame are directed/beam formed to one potential target only and the subsequent frames are directed/beam formed to other potential targets identified in the coarse target selection frame as shown in FIG. 4B, which shows a frame diagram 430 illustrating a sequence of transmitted chirps. Frame diagram 430 is similar to frame diagram 400 shown in FIG. 4A, with the exception that each presence detection frame occurring during second scanning 404 maintains a same beamforming configuration BF 1 to BF N during the presence detection frame instead of changing during the presence detection frame.

Figure 4C:
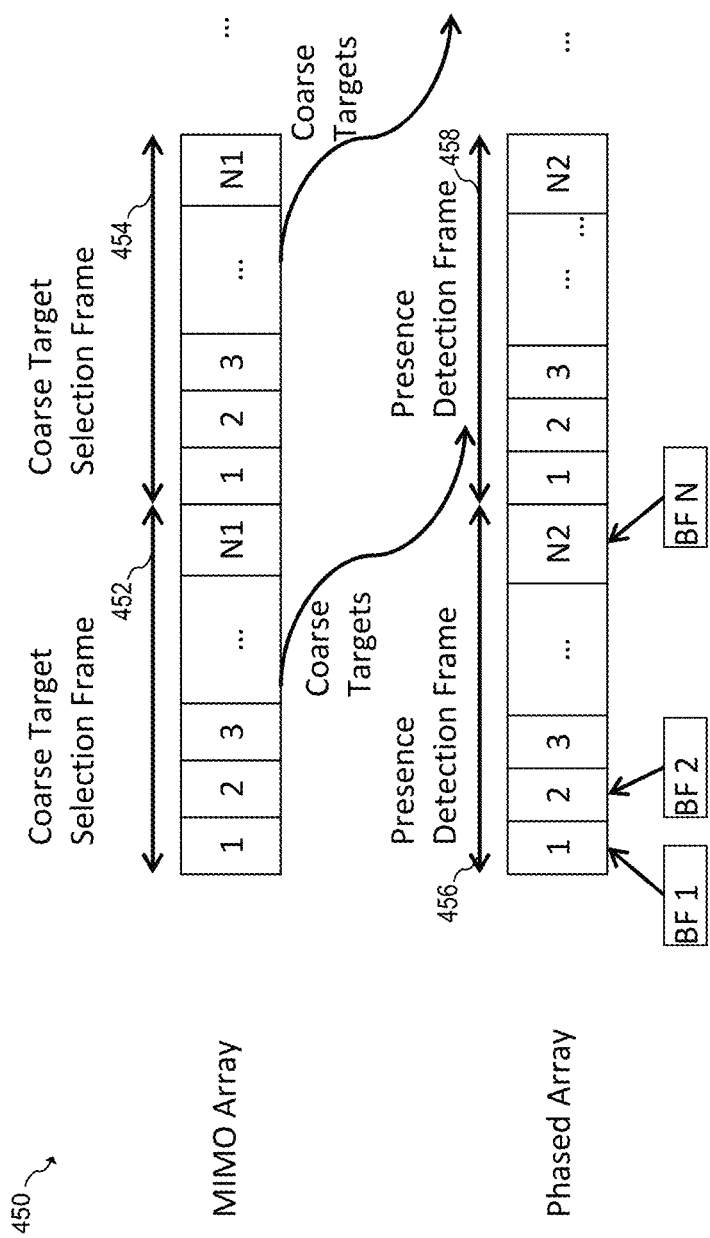

The frame structures shown in the FIGS. 4A and 4B are based on time multiplexing, however this frame structure can be extended to spatial multiplexing domain as well as shown in FIG. 4C. which frame diagram 450. In some embodiments, the presence detection system includes both a MIMO radar sensor array and a phased array radar sensor. The MIMO is used to perform coarse target selection, while the phased array radar sensor is used to perform presence detection as described above. By using separate MIMO and phased array radar sensor, coarse target selection and presence detection can be performed simultaneously. As shown, coarse target selection frame 452 performed by the MIMO radar sensor array occurs at the same time as presence detection from 456 performed by phased array radar sensor. Similarly, coarse target selection frame 454 performed by the MIMO radar sensor array occurs at the same time as presence detection from 458 performed by phased array radar sensor FIG. 4C shows a frame diagram 430 that illustrates a sequence of transmitted chirps according to a further embodiment of the present invention. As shown, the targets identified during selection frame 452 are further analyzed during subsequent present detection frames starting with presence detection frame 458. It should be understood that frame diagrams 400, 430 and 450 shown in FIGS. 4A, 4B and 4C is just a few examples of how embodiment presence detection frames can be organized.

Figure 5A:
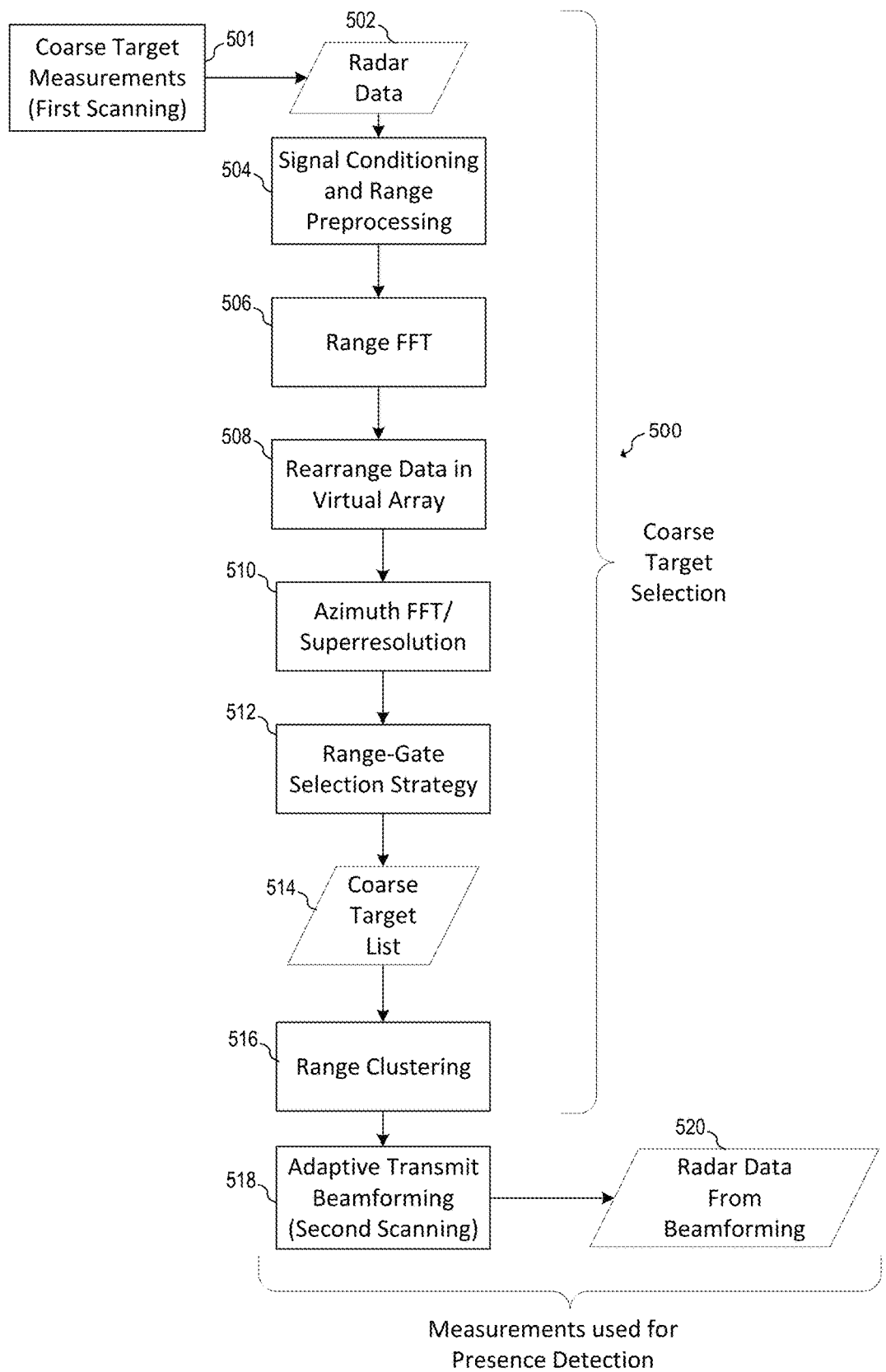
FIGS. 5A, 5B and 5C illustrate flow charts of embodiment occupancy detection methods.
Figure 5B:
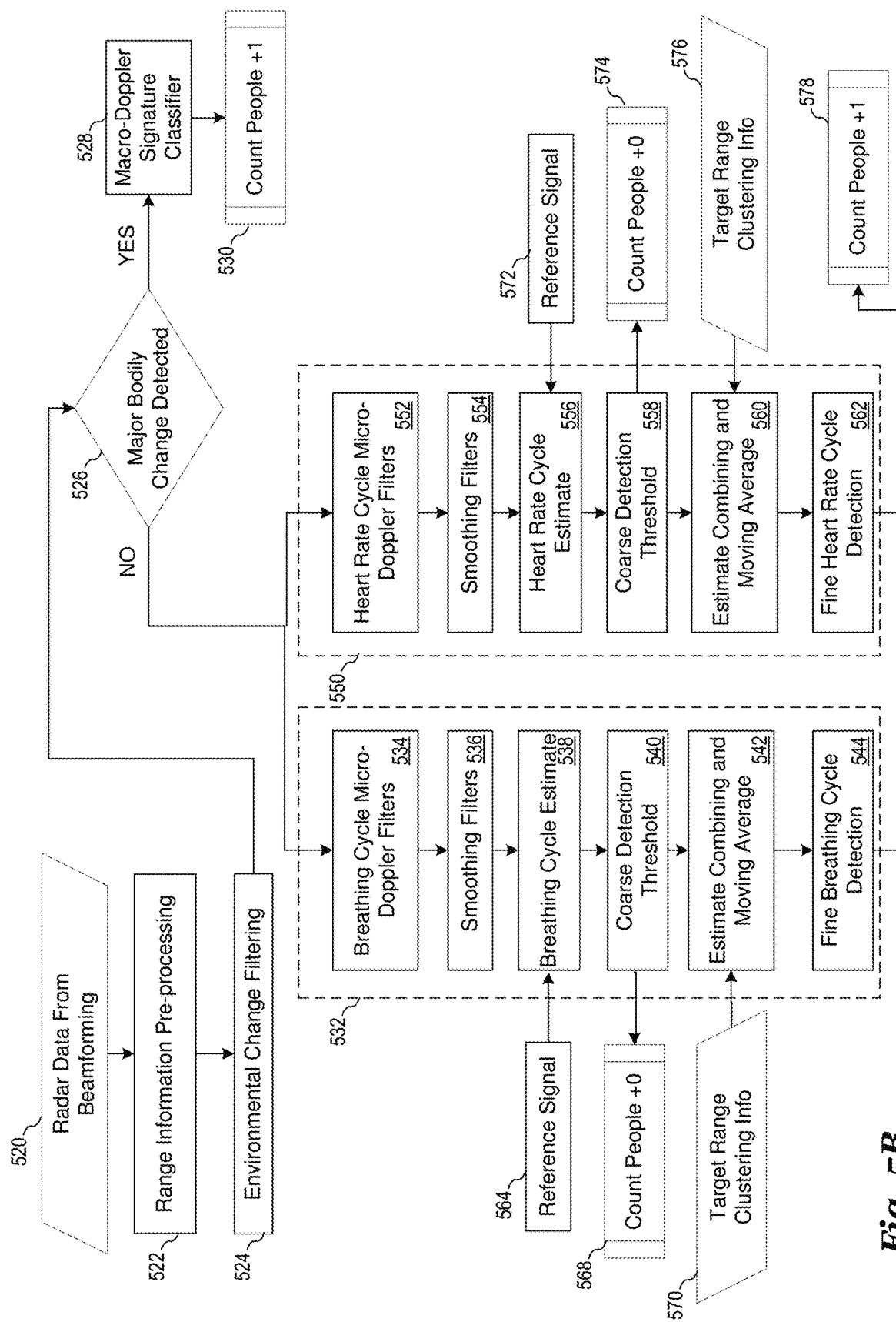
Figure 5C:
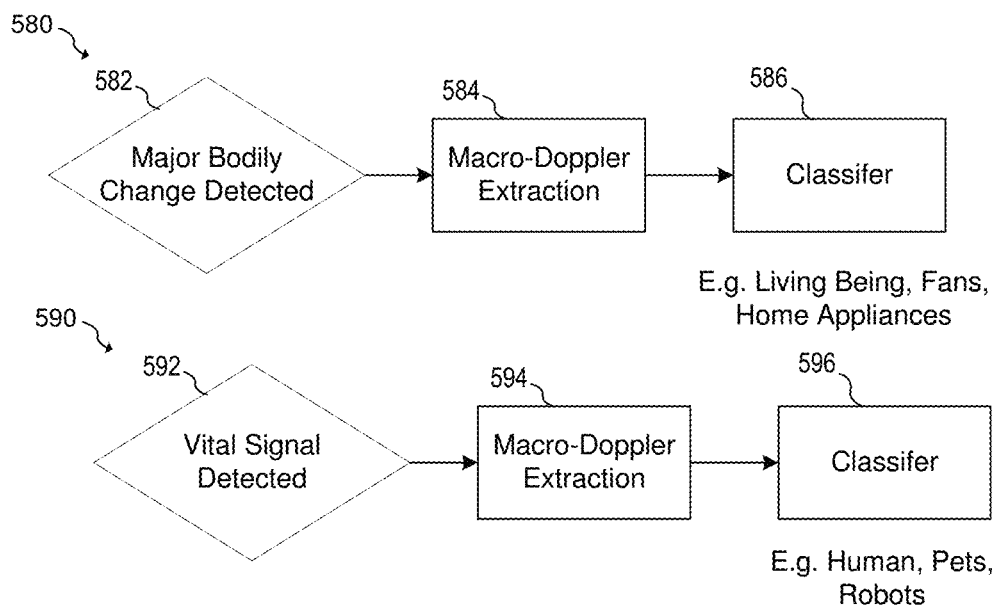

FIGS. 5A, 5B and 5C illustrate flowcharts of an embodiment occupancy detection method that can be used by the various embodiment occupancy detection systems disclosed herein. FIG. 5A covers steps performed during the coarse selection process 500 and adaptive transmit beam forming 518 up to the production of radar data from beamforming 520; FIG. 5B covers the presence detection process in which a number of humans are detected based on radar data from beamforming 520; and FIG. 5C illustrates embodiment classification methods.

Turning to FIG. 5A, the coarse target selection process 500 begins with a first scanning 501 that includes a series of coarse target selection measurements. In an embodiment, a series of chirps are transmitted and received by a millimeter-wave radar sensor, such as millimeter-wave radar sensors 102, 202, 220 and 232 shown in FIGS. 1A, 2A, 2B and 2C, respectively. These radar measurements, which can include baseband beat frequencies, are digitized and stored as radar data 502.

In step 504, signal conditioning and range preprocessing is performed. During step 504, radar data 502 is filtered, DC components are removed, and the IF data is cleared. In some embodiments, IF data is cleared by filtering to remove the Tx-Rx self-interference and optionally pre-filtering the interference colored noise. In some embodiments, filtering includes removing data outliers that have significantly different values from other neighboring range-gate measurements. In a specific example, a Hampel filter is applied with a sliding window at each range-gate to remove such outliers. Alternatively, other filtering for range preprocessing known in the art may be used.

In step 506 a range FFT is taken of the filtered radar data produced by step 504. In an embodiment, a windowed FFT having a length of the chirp (e.g., 256 samples) may be calculated along each waveform for the data resulting from the first scanning, or may be calculated for data corresponding to a portion of the first scanning performed during step 501. Each point of the range FFT represents a distance between the millimeter-wave sensor and a detected object and corresponds to a range gate. In some embodiments, a range FFT is performed for radar data produced by each receive antenna in a receive antenna array.

In step 508, the data produced by range FFT step 506 is rearranged in a virtual array. Here, multiple receiver data is stitched together for improved angular resolution using methods known in the art. In step 510, an azimuth FFT is performed on the virtual array data produced in step 508 using higher order beamforming and superresolution techniques known in the art. In various embodiments, the range FFT provides an indication as to the angular location of the detected objects with respect to the position of the millimeter-wave radar sensor. In alternative embodiments, other transform types could be used besides an FFT for the range and azimuth FFTs of steps 506 and 510, such as a Discrete Fourier Transform (DFT) or other transform types such as a z-transform.

In step 512 a range-gate selection strategy is implemented in order to determine which range-gates represent detected objects. In some embodiments, range-gates whose mean is greater than the mean of all the other range gates in its field of view are selected as potential target range-gates. In various embodiments, the range-gate selection strategy also determines the angle or azimuth of detected targets with respect to the millimeter-wave radar sensor as well as their range or distance to the millimeter-wave radar sensor. Once it is determined which range gates represent detected objects, a coarse target list 514 is produced that includes the range and azimuth of each detected object.

In step 516, clustering is performed on the detected objects in coarse target list 514. When a high-resolution radar is used, such as an embodiment millimeter-wave radar sensor, a single human target might be resolved into multiple ranges. These multiple ranges are grouped together clustering adjacent or nearest neighbor ranges. Such clustering of the detected range-gates/azimuths helps prevents the resolution a single target into multiple targets.

In step 518, a second scanning is performed in which a series of scans are directed toward the detected (and clustered) objects derived from coarse target list 514. During the second scanning, adaptive transmit beamforming/spatial filtering is performed in order to direct beams in the direction of the targets identified during coarse target selection step 500. Beamforming may be accomplished, for example, by transmitting different phases of the transmit signal via multiple transmit antennas. In some embodiments, beamforming may utilize discrete prolate spheroidal sequence (DPSS) methods or other beamforming methods known in the art. In some embodiments a series of scans or presence detection frames are performed in order to perform a directed measurement of each detected object. By using beamforming, isolated measurements of targets may be made and interference may be reduced from neighboring noise sources. The resulting radar measurements made during step 518 are stored as radar data from beamforming 520.

Continuing with FIG. 5B, which illustrates a method of presence detection process, range information preprocessing is performed on radar data from beamforming 520 during step 522. Range preprocessing may include removing data outliers that have significantly different values from other neighboring range-gate measurements in a manner similar to step 504 described above. For example, a Hampel filter may be applied with a sliding window at each range-gate to remove such outliers. Alternatively, other filtering for range preprocessing known in the art may be used.

In step 524, environmental change filtering is performed on the preprocessed radar data from beamforming 520. In an embodiment, a threshold-based approach is used to determine whether or not a segment of range-gate window measurements contains large body movement/environmental changes by examining the short-time energy of the moving variance of the range-gate. This variance energy may be empirically calculated in some embodiments. Range-gate measurements that fall below the threshold established by the short-time energy of the moving variance of the range-gate are considered to be representative of static objects, while range-gate measurements that are above the threshold are considered to be representative of moving objects or environmental changes. In some embodiments, previously measured vital measurements of objects that are determined to be moving objects are read off to take into disturbances and possible unreliability of vital data due to large movements. A separate environmental change filtering step may be performed for each presence detection frame. In some embodiments, additional range FFT and an azimuth FFTs are performed on the radar data from beamforming 520 during step 524 in order to determine the updated range-gates and direction of the target.

In step 526, it is determined whether a major bodily or environmental change is detected for a particular measured object based on the environmental change filtering in step 524. If a major bodily or environmental change is detected, a macro-Doppler signature classification operation 528 is performed on the presence sensing frame using for example, a machine learning algorithm such as, but not limited to a random forest algorithm, adaptive boosting (AdaBoost) algorithm and/or a neural network algorithm. If the characteristics of the macro-Doppler data match the characteristics of a human being, then the number of people in the area being analyzed is incremented in step 530.

If a major bodily or environmental change is not detected, a micro-Doppler extraction/filtering analyses are performed: a respiration micro-Doppler filtering analysis 532 and a heart rate micro-Doppler filtering analysis 550. In an embodiment, two fixed, calibrated low bandwidth filters are employed to extract a heart-beat signal and a breathing signal from the selected range gates. Radar data associated with static inanimate targets such as chairs, TV, etc., produce no vital signals after passing through these filters, whereas radar data associated with human targets produce vital signals after passing through these embodiment filters. Thus, the output of these filters can be used to determine whether or not radar data associated with a detected target corresponds with a human being. During the respiration micro-Doppler filtering analysis 532, motions corresponding to respiration are extracted from radar data from beamforming 520 in steps 534, 536, 538, 540, 542 and 544. In step 534, breathing cycle micro-Doppler filtering is performed. For example, the slow time radar signal from the specific/identified target range gate is fed into a band pass filter to determine the breathing rate. For example, a band-pass filter centered around 0.4 Hz with a bandwidth of 0.5 Hz can be used. Alternatively other center frequencies and bandwidths may be used.

In step 536, the output of micro-Doppler filtering step 534 is filtered using, for example, Savitzky-Golay filter to smooth the data. In step 538, the estimate of the breathing cycle is estimated, for example, by performing an autocorrelation of the output of the smoothing filter step 536 to determine the periodicity of the filtered micro-Doppler results. The result of this autocorrelation is compared with reference signal 564 that represents a nominal breathing rate. In some embodiments, the reference is a reference breathing signal. Alternatively, other references may be used. The estimated breathing cycle is compared to a threshold or a plurality of thresholds in step 540. If the estimated breathing cycle is not within a predetermined range that corresponds with a normal human respiration, for example, between about 12 breaths per minute and about 35 breaths per minute, then it is determined that the target is not human and the number of detected humans is not incremented (step 568). If the determined respiration is within the predetermined range, then the resulting estimate is averaged along with recent past measurements in step 542 using target ranged clustering information 570 and a moving average algorithm known in the art.

From the range clustering info all the corresponding range bins are fed into the breathing rate filter to analyze if they possess breathing rate signals. In various embodiments, the moving average represents between about one second and two seconds of filtered respiration measurements. Alternatively, the moving average may be performed over other time periods. Based on the result of the moving average produced by step 542, a fine breathing cycle is performed in step 544. In the fine breathing rate estimation cycle, more slow-time data is accumulated to get a finer estimate of the breathing rate. Alternatively, the breathing rate may be determined using an FFT method. For example, an FFT after windowing (Hanning or Kaiser window) is performed on the slow-time filtered breathing data. The coarse detection phase applies a threshold if there is a substantial breathing frequency component and the fine detection phase picks the maximum frequency component as the estimated breathing rate. The fine detection estimation phase may be skipped if the coarse threshold detection does not have a breathing frequency component that crosses the desired threshold.

During the heart rate micro-Doppler filtering analysis 550, motions corresponding to heart rate are extracted from radar data from beamforming 520 in steps 552, 554, 556, 558, 560 and 562 in a similar manner as breathing cycle micro-Doppler filtering analysis 532. In step 552, heart rate micro-Doppler filtering is performed. For example, the slow time radar signal from the specific/identified target range gate is fed into a band pass filter to determine the heart rate. In step 554, the output of micro-Doppler filtering step 552 is filtered using, for example, a lowpass filter to smooth the data. In step 556, the an estimate of the heart rate is estimated, for example, by performing an autocorrelation of the output of the smoothing filter step 554 to determine the periodicity of the filtered micro-Doppler results. The result of this autocorrelation is compared with reference signal 572 that represents a heart rate. In some embodiments, the reference is a standard FDA approved breathing signal of 60 beats/min. The estimated heart rate is compared with a threshold or a plurality of thresholds in step 558. If the estimated breathing cycle is not within a predetermined range that corresponds with a normal heart rate, for example, between about 50 beats per minute and about 200 beats per minute, then it is determined that the target is not human and the number of detected humans is not incremented (step 574). If the determined heart rate is within the predetermined range, then the resulting estimate is averaged along with recent past measurements in step 560 using target ranged clustering information 576 and a moving average algorithm known in the art.

From the range clustering info all the corresponding range bins are fed into the heart rate filter to analyze if they possess heart rate signals. In various embodiments, the moving average represents between about one second and two seconds of filtered heart rate measurements. Alternatively, the moving average may be performed over other time periods. Based on the result of the moving average produced by step 560, a fine heart rate detection is performed in step 562. In the heart rate estimation cycle, more slow-time data is accumulated to get a finer estimate of the heart rate. Alternatively, the heart rate may be determined using an FFT method. For example, an FFT after windowing (Hanning or Kaiser window) is performed on the slow-time filtered heart rate data. The coarse detection phase applies a threshold if there is a substantial heart rate frequency component and the fine detection phase picks the maximum frequency component as the estimated heart rate. The fine detection estimation phase may be skipped if the coarse threshold detection does not have a heart rate frequency component that crosses the desired threshold.

If both breathing cycle micro-Doppler filtering analysis 532 and heart rate micro-Doppler filtering analysis 550 determine that the respective estimated breathing cycle and heart rate measurements are within a predetermined ranged, the number of people detected is incremented in step 578. Alternatively, the number of people detected if at least one of the breathing cycle and the heart rate is determined to be within a range of a human being.

FIG. 5C illustrates flow charts of embodiment classification methods that may be used to classify detected targets. More specifically, method 580 is a method of classifying detected targets based on a major bodily change and method 590 is a method of classifying detected targets based on detected vital signals.

In step 582 of method 580, it is determined whether a major bodily change is detected. If so, a macro-Doppler extraction is performed in step 584 and a classification algorithm is performed such as, but not limited to a random forest algorithm, adaptive boosting (AdaBoost) algorithm and/or a neural network algorithm to determine the identification of the detected object in step 586. Examples of moving objects that may be detected on the basis of its detected motion include, but are not limited to living beings, swinging or rocking objects such as chairs or moving light fixtures, home appliances and other machinery. Method 580 may be used to implement steps 526 and 528 shown in FIG. 5B.

Method 590 is performed at the output of breathing cycle micro-Doppler filters and heart-rate cycle micro-Doppler filters. Both the filter outputs can be used together as a feature vectors for the micro-Doppler classifier. In an alternative embodiment, a single wider bandwidth micro-Doppler filter (super-set of breathing rate filter and heart rate filter) can be used to input in the micro-Doppler classifier. In step 592 of method 590, vital signals are detected. Such a detection may accomplished using respiration micro-Doppler filtering analysis 532 and heart rate micro-Doppler filtering analysis 550 described above with respect to FIG. 5B. If vital signals are detected in step 592, then a macro-Doppler extraction is performed in step 594 and a classification algorithm 596 is performed such as, but not limited to a random forest algorithm, adaptive boosting (AdaBoost) algorithm and/or a neural network algorithm to determine the identification of the detected object. Examples of objects that may be detected by classification algorithm 596 include, but are not limited to living beings, such as humans and animals, or non-human beings, such as robots.

Figure 6:
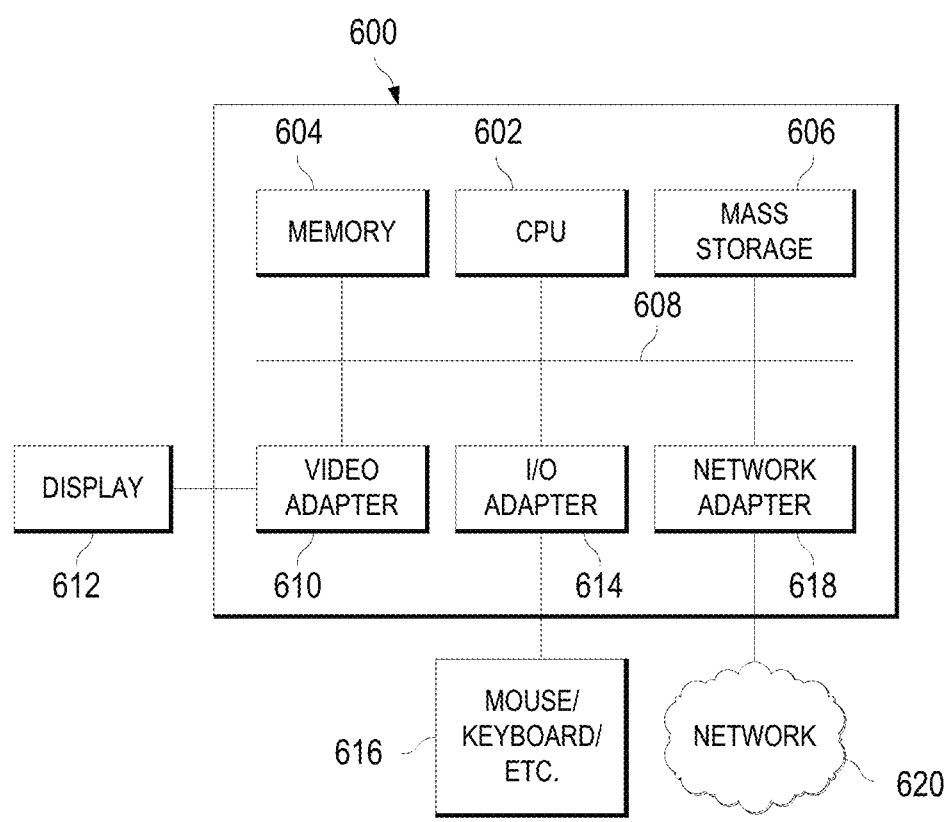
FIG. 6 illustrates a block diagram of a processing system that may be used to implement portions of embodiment occupancy detection systems.

Referring now to FIG. 6, a block diagram of a processing system 600 is provided in accordance with an embodiment of the present invention. The processing system 600 depicts a general-purpose platform and the general components and functionality that may be used to implement portions of the embodiment occupancy detection system and/or an external computer or processing device interfaced to the embodiment occupancy detection system. The processing system 600 may include, for example, a central processing unit (CPU) 602, memory 604, and a mass storage device 606 connected to a bus 608 configured to perform the processes discussed above. The processing system 600 may further include, if desired or needed, a video adapter 610 to provide connectivity to a local display 612 and an input-output (I/O) Adapter 614 to provide an input/output interface for one or more input/output devices 616, such as a mouse, a keyboard, printer, tape drive, CD drive, or the like.

The processing system 600 also includes a network interface 618, which may be implemented using a network adaptor configured to be coupled to a wired link, such as an Ethernet cable, USB interface, or the like, and/or a wireless/cellular link for communications with a network 620. The network interface 618 may also comprise a suitable receiver and transmitter for wireless communications. It should be noted that the processing system 600 may include other components. For example, the processing system 600 may include power supplies, cables, a motherboard, removable storage media, cases, and the like. These other components, although not shown, are considered part of the processing system 600.

Example embodiments of the present invention are summarized here. Other embodiments can also be understood from the entirety of the specification and the claims filed herein.

Example 1

A method for presence detection including: performing a first scanning that includes scanning a first area using a millimeter-wave radar sensor to produce a first set of radar data; identifying a first set of targets based on the first set of radar data; performing a second scanning comprising scanning portions of the first area corresponding to the first set of targets using the millimeter-wave radar sensor, and performing micro-Doppler measurements on the portions of the first area; detecting vital signals of targets of the first set of targets from the micro-Doppler measurement; and determining which targets of the first set of targets meet a first set of criteria based on the detected vital signals.

Example 2

The method of example 1, where performing the first scanning further includes performing macro-Doppler measurements on the first set of targets.

Example 3

The method of one of example 1 or 2, where the vital signals include heart rate and respiration.

Example 4

The method of example 3, where determining which targets of the first set of targets meet a first set of criteria include determining which targets of the first set of targets are human based on the detected vital signals.

Example 5

The method of example 4, further including determining a number of detected humans based on the detected vital signals.

Example 6

The method of one of examples 4 or 5, where determining which targets of the first set of targets are human based on the detected vital signals includes determining whether the heart rate and respiration of each target is within a predetermined range.

Example 7

The method of one of examples 1-6, where identifying the first set of targets includes identifying range-gates having a mean greater than a mean of all other range-gates to form a set of identified range-gates.

Example 8

The method of claim 7, where identifying the first set of targets includes clustering adjacent identified range gates into a single identified target.

Example 9

The method of one of examples 1-8, where performing the second scanning comprises using transmit beamforming to direct a radar beam of the millimeter-wave radar sensor toward the portions of the first area corresponding to the first set of targets.

Example 10

A system including: a processing system configured to be coupled to a millimeter-wave radar sensor, the processing system configured to instruct the millimeter-wave radar sensor to perform a first scanning that includes scanning a first area using a millimeter-wave radar sensor to produce a first set of radar data; identifying a first set of targets based on the first set of radar data; instruct the millimeter-wave radar sensor to perform a second scanning comprising scanning portions of the first area corresponding to the first set of targets using the millimeter-wave radar sensor, and perform micro-Doppler measurements on the portions of the first area; detect vital signals of targets of the first set of targets from the micro-Doppler measurement; and determine which targets of the first set of targets meet a first set of criteria based on the detected vital signals.

Example 11

The system of example 10, further including the millimeter-wave radar sensor.

Example 12

The system of one of examples 10 and 11, where the millimeter-wave radar sensor includes: a plurality of receive antennas coupled to a corresponding plurality of RF receive circuits; and a plurality of transmit antennas coupled to a corresponding plurality of RF transmit circuits.

Example 13

The system of example 12, wherein during the second scanning, the processing system is further configured to instruct the millimeter-wave radar sensor to direct a radar beam toward the portions of the first area corresponding to the first set of targets using the plurality of transmit antennas.

Example 14

The system of one of examples 10-13, where the plurality of receive antennas and the plurality of transmit antennas are arranged to meet a predetermined a field of view and azimuth-elevation resolution specification.

Example 15

The system of one of examples 10-14, where the processing system is further configured to perform macro-Doppler measurements on the first set of targets to determine which of the first set of targets are moving.

Example 16

The system of one of examples 10-15, where the detected vital signals comprise heart rate and respiration.

Example 17

The system of example 16, where the processing system is further configured to determine which targets of the first set of targets meet a first set of criteria by determining which targets of the first set of targets are human based on the detected vital signals.

Example 18

The system of example 17, wherein the processing system is further configured to determine a number of detected humans based on the detected vital signals.

Example 19

The system of one of examples 17 or 18, where: the processing system is further configured to perform macro-Doppler measurements on the first set of targets; and determining which targets of the first set of targets are human further comprises applying a classification algorithm to the macro-Doppler measurements.

Example 20

The system of one of examples 17-19, where the processing system is configured to determine which targets of the first set of targets are human based on the detected vital signals by determining whether the heart rate and respiration of each target is within a predetermined range.

Example 21

The system of one of examples 10-20 claim 10, where the processing system is configured to identify the first set of targets by identifying range-gates having a mean greater than a mean of all other range-gates to form a set of identified range-gates.

Example 22

The system of example 21, where the processing system is configured to identify the first set of targets by clustering adjacent identified range gates into a single identified target.

Example 23

A non-transitory computer readable storage medium with an executable program stored thereon, the executable program including instructions to: instruct a millimeter-wave radar sensor to perform a first scanning that includes scanning a first area using a millimeter-wave radar sensor to produce a first set of radar data; identify a first set of targets based on the first set of radar data; instruct the millimeter-wave radar sensor to perform a second scanning comprising scanning portions of the first area corresponding to the first set of targets using the millimeter-wave radar sensor, and perform micro-Doppler measurements on the portions of the first area; and determine which targets of the first set of targets are human based on the micro-Doppler measurements.

Example 24

The non-transitory computer readable storage medium of example 23, where: the executable program including further includes instructions to detect vital signals of targets of the first set of targets from the micro-Doppler measurements; the detected vital signals comprise heart rate and respiration; and determining which targets of the first set of targets are human includes determining whether the heart rate and respiration of each target is within a predetermined range.

Example 25

The non-transitory computer readable storage medium of one of examples 23 or 24, where the executable program is further configured to instruct the millimeter-wave radar sensor to direct a radar beam toward the portions of the first area corresponding to the first set of targets using the plurality of transmit antennas during the second scanning.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for presence detection, the method comprising:
performing a first scanning comprising scanning a first area using a millimeter-wave radar sensor to produce a first set of radar data;
identifying a first set of targets based on the first set of radar data;
performing a second scanning comprising scanning portions of the first area corresponding to the first set of targets using the millimeter-wave radar sensor, and performing micro-Doppler measurements on the portions of the first area, wherein performing the second scanning comprises using transmit beamforming to direct a radar beam of the millimeter-wave radar sensor toward the portions of the first area corresponding to the first set of targets;
detecting vital signals of targets of the first set of targets from the micro-Doppler measurement; and
determining which targets of the first set of targets meet a first set of criteria based on the detected vital signals.

2. The method of claim 1, wherein performing the first scanning further comprises performing macro-Doppler measurements on the first set of targets.

3. The method of claim 1, wherein the vital signals comprise heart rate and respiration.

4. The method of claim 3, wherein determining which targets of the first set of targets meet the first set of criteria comprises determining which targets of the first set of targets are human based on the detected vital signals.

5. The method of claim 4, further comprising determining a number of detected humans based on the detected vital signals.

6. The method of claim 4, wherein determining which targets of the first set of targets are human based on the detected vital signals comprises determining whether the heart rate and respiration of each target is within a predetermined range.

7. The method of claim 1, wherein identifying the first set of targets comprises identifying range-gates having a mean greater than a mean of all other range-gates to form a set of identified range-gates.

8. The method of claim 7, wherein identifying the first set of targets comprises clustering adjacent identified range gates into a single identified target.

9. A system comprising:
a processing system configured to be coupled to a millimeter-wave radar sensor, the processing system configured to
instruct the millimeter-wave radar sensor to perform a first scanning comprising scanning a first area using the millimeter-wave radar sensor to produce a first set of radar data;
identifying a first set of targets based on the first set of radar data;
instruct the millimeter-wave radar sensor to perform a second scanning comprising scanning portions of the first area corresponding to the first set of targets using the millimeter-wave radar sensor, and perform micro-Doppler measurements on the portions of the first area, wherein during the second scanning, the processing system is further configured to instruct the millimeter-wave radar sensor to direct a radar beam toward the portions of the first area corresponding to the first set of targets using transmit beamforming via a plurality of transmit antennas;
detect vital signals of targets of the first set of targets from the micro-Doppler measurement; and
determine which targets of the first set of targets meet a first set of criteria based on the detected vital signals.

10. The system of claim 9, further comprising the millimeter-wave radar sensor.

11. The system of claim 10, wherein the millimeter-wave radar sensor comprises:
a plurality of receive antennas coupled to a corresponding plurality of RF receive circuits; and
the plurality of transmit antennas coupled to a corresponding plurality of RF transmit circuits.

12. The system of claim 10, wherein the plurality of receive antennas and the plurality of transmit antennas are arranged to meet a predetermined a field of view and azimuth-elevation resolution specification.

13. The system of claim 9, wherein the processing system is further configured to perform macro-Doppler measurements on the first set of targets to determine which of the first set of targets are moving.

14. The system of claim 9, wherein the detected vital signals comprise heart rate and respiration.

15. The system of claim 14, wherein the processing system is further configured to determine which targets of the first set of targets meet the first set of criteria by determining which targets of the first set of targets are human based on the detected vital signals.

16. The system of claim 15, wherein the processing system is further configured to determine a number of detected humans based on the detected vital signals.

17. The system of claim 15, wherein:
the processing system is further configured to perform macro-Doppler measurements on the first set of targets; and
determining which targets of the first set of targets are human further comprises applying a classification algorithm to the macro-Doppler measurements.

18. The system of claim 15, wherein the processing system is configured to determine which targets of the first set of targets are human based on the detected vital signals by determining whether the heart rate and respiration of each target is within a predetermined range.

19. The system of claim 9, wherein the processing system is configured to identify the first set of targets by identifying range-gates having a mean greater than a mean of all other range-gates to form a set of identified range-gates.

20. The system of claim 19, wherein the processing system is configured to identify the first set of targets by clustering adjacent identified range gates into a single identified target.

21. A non-transitory computer readable storage medium with an executable program stored thereon, the executable program including instructions to:
instruct a millimeter-wave radar sensor to perform a first scanning comprising scanning a first area using the millimeter-wave radar sensor to produce a first set of radar data;
identify a first set of targets based on the first set of radar data;
instruct the millimeter-wave radar sensor to perform a second scanning comprising scanning portions of the first area corresponding to the first set of targets using the millimeter-wave radar sensor, and perform micro-Doppler measurements on the portions of the first area, wherein the executable program is further configured to instruct the millimeter-wave radar sensor to direct a radar beam toward the portions of the first area corresponding to the first set of targets using transmit beamforming via a plurality of transmit antennas during the second scanning; and
determine which targets of the first set of targets are human based on the micro-Doppler measurements.

22. The non-transitory computer readable storage medium of claim 21, wherein:
the executable program including further includes instructions to detect vital signals of targets of the first set of targets from the micro-Doppler measurements;
the detected vital signals comprise heart rate and respiration; and
determining which targets of the first set of targets are human comprises determining whether the heart rate and respiration of each target is within a predetermined range.

* * * * *